(12) United States Patent
Datla et al.

(10) Patent No.: US 12,286,454 B2
(45) Date of Patent: Apr. 29, 2025

(54) IRRADIATION PROCESS OF PRO VITAMIN D

(71) Applicant: FERMENTA BIOTECH LIMITED, Thane (IN)

(72) Inventors: Anupama Datla, Thane (IN); Prashant Nagre, Thane (IN); Jagdish Tamore, Thane (IN); Sreenath Trivikram, Dombivli (IN); Sachin Wadhavane, Navi Mumbai (IN)

(73) Assignee: FERMENTA BIOTECH LIMITED, Thane (IN)

( * ) Notice: Subject to any disclaimer, the term of this patent is extended or adjusted under 35 U.S.C. 154(b) by 303 days.

(21) Appl. No.: 17/609,627

(22) PCT Filed: May 11, 2020

(86) PCT No.: PCT/IN2020/050426
§ 371 (c)(1),
(2) Date: Nov. 8, 2021

(87) PCT Pub. No.: WO2020/230159
PCT Pub. Date: Nov. 19, 2020

(65) Prior Publication Data
US 2022/0234972 A1    Jul. 28, 2022

(30) Foreign Application Priority Data
May 10, 2019   (IN) .............................. 201921018751

(51) Int. Cl.
C07J 15/00     (2006.01)
A61K 31/593    (2006.01)
C07C 401/00    (2006.01)
C07J 9/00      (2006.01)

(52) U.S. Cl.
CPC ............ *C07J 15/005* (2013.01); *A61K 31/593* (2013.01); *C07C 401/00* (2013.01); *C07J 9/00* (2013.01)

(58) Field of Classification Search
CPC ......... C07J 9/00; C07J 15/005; C07C 401/00; A61K 31/593
See application file for complete search history.

(56) References Cited

U.S. PATENT DOCUMENTS

| | | | |
|---|---|---|---|
| 3,176,029 A | 3/1965 | Bharucha et al. | |
| 3,661,939 A | 5/1972 | Toyoda et al. | |
| 6,180,805 B1 | 1/2001 | Jansen | |
| 2017/0369436 A1 | 12/2017 | Treiber | |

FOREIGN PATENT DOCUMENTS

| | | |
|---|---|---|
| CN | 1033993 | 7/1989 |
| IN | 48/2019 A | 11/2019 |
| WO | 2008128783 A2 | 10/2008 |

OTHER PUBLICATIONS

CN1033993A translation, Jul. 19, 1989.

*Primary Examiner* — Barbara P Badio
(74) *Attorney, Agent, or Firm* — Kramer & Amado P.C.

(57) ABSTRACT

The invention discloses an improved process for production of vitamin D3 from 7-dehydrocholesterol (7-DHC) and to a simple process for recovery unreacted 7-DHC for further reuse. The invention further describes a process for isolation and purification of Vitamin D3.

18 Claims, No Drawings

IRRADIATION PROCESS OF PRO VITAMIN D

TECHNICAL FILED

The invention relates to an improved process for production of vitamin D3 from 7-dehydrocholesterol (7-DHC) and to a simple process for recovery unreacted 7-DHC for further reuse. The invention further relates to a process for isolation and purification of Vitamin D3.

BACKGROUND AND PRIOR ART

Conventionally, Vitamin D3 has been produced by an irradiation of 7-dehydrocholesterol with ultraviolet rays in an organic solvent. In such a process, however, there are disadvantages that the solubility of 7-dehydrocholesterol in many organic solvents is less and as a result an effective irradiation of 7-dehydrocholesterol using ultraviolet rays is difficult to achieve and hence pose a challenge to scale up such processes for industrial production of Vitamin D. Accordingly various organic solvents have been studied as a medium for irradiating 7-dehydrocholesterol.

Another drawback is that the starting material (7-DHC), the primary product (pre vitamin D3) as well as by products, absorb with different efficiency in the same UV wavelength range, favours the formation of photochemical by products such as lumisterol and tachysterol which are inactive and in some cases toxic also. Therefore, it is necessary to interrupt the irradiation after relatively low conversion of the 7-DHC to D3. The unconverted 7-DHC is recycled while the primary product (Vitamin D3) is purified.

Moreover vitamin D2 and D3 are also not stable in solutions as they exhibit reversible thermal isomerization to their corresponding pre-vitamins forming equilibrium mixtures. Further, vitamin D2 and D3 are susceptible to decomposition in presence of oxygen and light.

There are few prior art reports available on manufacturing process of vitamin D3, which are as follows.

U.S. Pat. No. 3,176,029A discloses a process for the treatment of the irradiation products of 7-dehydrocholesterol, comprising: treating said irradiation products with ethanol to remove a portion of the unreacted pro-vitamin and provide a residual ethanol gum, dissolving said ethanol gum in methanol, precipitating an adduct of vitamin D3 and pro-vitamin from the methanol solution, and separating said precipitated adduct from said solution.

U.S. Pat. No. 3,661,939 discloses a process for the production of a mixture containing vitamin D3 wherein a solution of 7-dehydrocholesterol organic acid ester in an organic solvent is irradiated with ultraviolet rays to obtain a mixture containing pre-vitamin D3 organic acid ester and then said mixture containing pre-vitamin D3 organic acid ester is subjected to a saponification and heating operation to obtain a mixture containing vitamin D3.

WO2008128783A2 discloses a photochemical process for the preparation of a pre-vitamin D or a derivative thereof from a 7-dehydrosterol or a corresponding derivative thereof which process comprises irradiating the 7-dehydrosterol or the derivative thereof with UV LED(s).

CN1033993A discloses a method of synthesis of vitamin D characterized in that: the use of a YAG laser with a wavelength of 266 nm and 355 nm laser irradiation alternately in two or pro-vitamins ergosterol (E) or 7-dehydro-cholesterol (7-DHC), to synthesize vitamin D2 or vitamin D3.

U.S. Pat. No. 6,180,805B1 discloses a photochemical process for the production of previtamin D3 or a derivative thereof from 7-dehydrocholesterol which comprises:
(a) irradiating 7-dehydrocholesterol in a falling film reactor with a UV radiation source, wherein the UV radiation source comprises an excimer or exciplex emitter containing XeBr which emits quasi-monochromatically according to the corona discharge mechanism in the UV range; and
(b) recovering the previtamin D3 or derivative thereof.

US20170369436 discloses a method of production of vitamin-D2 using ergosterol or a dihydroxy derivative thereof as a starting material, or production of vitamin-D3 using 7-dehydrocholesterol or a dihydroxy derivative thereof as the starting material, comprising:
(a) irradiating the starting material in a solution comprising an organic or inorganic base with ultraviolet light to obtain a product containing pre-vitamin-D2 or pre-vitamin-D3, and
(b) heating the product to convert the pre-vitamin-D2 or pre-vitamin-D3 to vitamin D2 or vitamin D3.

The teachings of US'946 is incomplete in view of the percentage conversions and purity of the Vitamin D2 and Vitamin D3. Although demonstrated the irradiation process with very few organic bases, however, fails to provide the applicability of the same with other organic and inorganic bases.

In the light of the above, it is evident that the products of irradiation processes are of widely varying in composition and the quantity of Vitamin D3 depends on the extent of photochemical reaction and the purity of the end product.

Therefore, there remains a need in the art to provide an improved irradiation conditions for production of Vitamin D3 from 7-DHC and for simplified process for recovery unreacted 7-DHC from the reaction mass, which becomes an objective of the present invention, for which protection is sought.

SUMMARY OF THE INVENTION

In the light of the above, the present invention provides a photochemical process for the preparation of a vitamin D3 or a derivative thereof which process comprises irradiating 7-dehydrosterol in combination with a sterol derivative and anti-oxidant in presence of an alkali.

Accordingly, the photochemical process for the preparation of a vitamin D3 which process comprises;
a) Heating the mixture of 7-dehydrocholesterol in combination with a sterol derivative in presence of catalytic amounts of an anti-oxidant and an alkali in an organic solvent at a temperature range of 20-85° C.;
b) Irradiating the mixture using a low pressure Mercury lamp at 10-85° C.; and
c) Isolating and purifying vitamin D3 from the irradiated mixture.

In another aspect, the invention provides process for isolation and purification of Vitamin D3.

DETAILED DESCRIPTION OF THE INVENTION

The invention will now be described in detail in connection with certain preferred and optional embodiments, so that various aspects thereof may be more fully understood and appreciated.

Accordingly, the present invention provides a photochemical process for the preparation of a vitamin D3 or a derivative thereof which process comprises irradiating the 7-dehydrocholesterol in combination with corresponding derivative thereof in ethanol and in presence of anti-oxidant and an alkali.

The samples of 7-dehydrocholesterol, the starting material used in the present invention is synthesised from Cholesterol isolated either from wool grease which is sourced from New Zealand or Fish oil sourced from Chile or Milk fat sourced from Europe. The Cholesterol used for the synthesis of 7-dehydrocholesterol, the starting material, is isolated from Wool grease, which is sourced from New Zealand.

Accordingly, the photochemical process for the preparation of a vitamin D3 which process comprises;
a) Heating the mixture of 7-dehydrocholesterol in combination with a sterol derivative in presence of catalytic amounts of an anti-oxidant and an alkali in an organic solvent at a temperature range of 20-85° C.;
b) Irradiating the mixture using a low pressure Mercury lamp at 10-85° C.; and
c) Isolating and purifying vitamin D3 from the irradiated mixture.

The sterol derivative is selected from the group consisting of Cholesterol, Phytosterol, Lanosterol, etc. 7-Dehydrocholesterol is charged with sterol derivative approximately in a ratio of 1:0.1 to 1:3.

The organic solvent in step a) may be selected from the group consisting of methanol, ethanol, Isopropanol, Tetrahydrofuran, Diethyl ether, methyl-tert-butyl ether, methyl isobutyl ketone & petroleum Ether (40-60° C. & 60-80° C.).

The use of sterol derivative is to facilitate the solidification of the unreacted 7-DHC from the resinous reaction mass thereby simplifying the recovery and reuse of 7-DHC in the subsequent batch. The use of sterol derivative further makes the isolation of Vitamin D3 less cumbersome.

The anti-oxidant is preferably selected from Butylated hydroxyl toluene, propyl gallate, butylated hydroxyanisole etc. One preferable antioxidant is Butylated hydroxyl toluene.

The alkali is selected from the group consisting of sodium hydroxide, potassium hydroxide, lithium hydroxide or ammonia. In one preferred embodiment, the alkali is preferably 2% to 10% of sodium hydroxide.

The reaction mass is irradiated by a low pressure Mercury lamp at 80-85° C. for 30-300 minutes preferably 60-240 minutes or more preferably 100-200 minutes to accomplish the reaction.

The isolation and purification of vitamin D3 comprises the steps of;
a) Repeatedly cooling the reaction mass to 0-45° C. ° C. to separate the solids consisting of 7-DHC and sterol derivative followed by concentrating the filtrate under vacuum to obtain concentrated mass;
b) Adding an organic solvent to the mass of step a) followed by washing with aq. Ethanol and further distillation under vacuum to obtain residue;
c) Adding an organic solvent to residue followed by cooling up to −5° C.-+35° C. to separate the solids consisting of Vitamin D3, 7-Dehydrocholesterol and sterol derivative;
d) Evaporating the filtrate under vacuum at 40-45° C. to obtain crude Vitamin D3 (resin); and
e) Purifying the crude vitamin D3 by converting into its ester followed by saponification and crystallization from an organic solvent to obtain pure vitamin D3.

The organic solvent used in step b) is selected from the group consisting of methyl tert butyl ether, petroleum ether (40-60° C. & 60-80° C.), n-Heptane, n-Hexane, ethyl acetate, Diethyl ether, Toluene and Xylene.

The organic solvent used for crystallization in step c) is selected from the group consisting of 2-Butanone, Acetone, Methyl-Isobutyl ketone, petroleum ether (40-6-° C. &60-80° C.), n-heptane or n-Hexane.

The solids obtained in steps a) and c) according to the process are collected and reused in the subsequent batch.

The esters of vitamin D3 are selected from the group consisting of Acetate, Propionate, Butyrate, Valerate, 2-Nitrobenzoate or 4-Nitrobenzoate, more preferably Butyrate and can be prepared by treating the crude with the respective acids or anhydrides.

The saponification of the ester is carried out using a base selected from Sodium Hydroxide, Potassium hydroxide, Sodium carbonate, Potassium carbonate, Sodium methoxide, Sodium Ethoxide, Potassium butoxide or Lithium Aluminium Hydride.

The organic solvent used for crystallization of vitamin D3 in step e) is a ketone or an ester selected from the group consisting of acetone, 2-Butanone, Methyl isobutyl ketone, methyl formate, ethyl formate.

In an alternate embodiment, the residue obtained in step b) may be purified directly by column chromatography over silica gel or neutral Alumina or Alumina with 2-10% water, by eluting with Toluene: 2-Butanone in a ratio of 1:99, 2:98, 4:96 & 5:95 to isolate pure Vitamin D3/Cholecalciferol crystals. Alternately, pure Vitamin D3/Cholecalciferol crystals can be obtained by eluting with Dichloromethane: methanol 99:1, 98:2, 95:5, 90:10 or with Ethyl Acetate: methanol 99:1, 98:2, 95:5 & 90:10.

In yet another embodiment, the invention provides a composition which comprises:
a) Vitamin D3 in about 98-99.5%; and
b) one or both of lumisterol and tachysterol at a concentration of at least 0.02% of the vitamin D3 present in the composition;
c) Trans Vitamin D3 at a concentration of at least 0.05%;
Wherein, the vitamin D3 meets potency requirement of 40 MIU.

Accordingly in one preferred embodiment, 7-Dehydrocholesterol is charged with cholesterol approximately in the ratio of 1:0.1 to 1:3 along with catalytic amounts of Butylated hydroxyl toluene as an anti-oxidant and 2 to 10% of aq. Sodium hydroxide solution in Ethanol and heated the reaction mass at a temperature range of 0-90° C. preferably at 20-85° C. or more preferably 75-85° C. The reaction mass is then irradiated by a low pressure Mercury lamp at 80-85° C. for 30-300 minutes preferably, 60-240 minutes or more preferably 100-200 minutes. The reaction mass is further cooled to −10-50° C., preferably to 15-30° C. or most preferably to 0-5° C.

The solids separated out are filtered which contains 7-Dehydrocholesterol and Cholesterol which is the $1^{st}$ crop.

The filtrate is concentrated to 5-50% of the original volume preferably 10-40% or more preferably 10-20% of the original volume, cooled to 10-15° C. and the separated solids are filtered that contains 7-Dehydrocholesterol and Cholesterol, which is the $2^{nd}$ crop.

The filtrate is again concentrated under vacuum and methyl tert butyl ether is added and washed with 1:1 alcohol and water and further distilled under vacuum to obtain a residue, wherein the alcohol is selected from methanol, ethanol and isopropanol. An organic solvent selected from 2-Butanone (methyl ethyl ketone), Methyl isobutyl ketone, methyl formate or ethyl formate is added to the residue, cooled the mass in the temperature range of −5° C.-+35° C.

and the separated solids are filtered which contains Vitamin D3, 7-Dehydrocholesterol and Cholesterol, which is the 3$^{rd}$ crop. These solids obtained in 1$^{st}$, 2$^{nd}$ and 3$^{rd}$ crops are reused in subsequent batches for the irradiation to obtain vitamin D3.

The filtrate is then evaporated under vacuum at 40-45° C. and the crude Vitamin D3 (resin) is analysed and the results are shown in table 1.

In an alternate embodiment, after removal of the first crop (unreacted 7-DHC and Cholesterol), the filtrate is concentrated under vacuum and the residue is dissolved in Methyl tert butyl ether, washed with 10×100 ml 1:1 ethanol water and distilled under vacuum. The residue is purified by column chromatography over silica gel with Toluene:methyl ethyl ketone 1:99, 2:98, 4:96 & 5:95 to isolate pure Vitamin D3/Cholecalciferol crystals. The results are shown in table 4.

In another preferred embodiment, 7-Dehydrocholesterol is charged with Phytosterol approximately in the ratio of 1:0.1 to 1:3 along with catalytic amounts of Butylated hydroxyl toluene as an anti-oxidant and 2 to 10% of Aq. Sodium hydroxide solution in Ethanol and heated the reaction mass at a temperature range of 0-90° C. preferably at 20-85° C. The reaction mass is then irradiated by a low pressure Mercury lamp at 75-85° C. for 30-300 minutes preferably 60-240 minutes or more preferably 100-200 minutes. The reaction mass is cooled to −10 to 50° C. preferably to 15-30° C. or more preferably to 0-5° C. The solids separated out are filtered which contains 7-Dehydrocholesterol and Phytosterol which is the 1st crop.

The filtrate is concentrated to 5-50% of the original volume preferably 10-40% or more preferably 10-20% of the original volume, cooled to 10-15° C. and the separated solids are filtered that contains 7-Dehydrocholesterol and Phytosterol, which is the 2nd crop.

The filtrate is again concentrated under vacuum and methyl tert butyl ether is added and washed with 1:1 ethanol water and distilled under vacuum. 2-Butanone (methyl ethyl ketone) is added to the residue, cooled to (−5) to (−8)° C. and the separated solids are filtered which contains Vitamin D3, 7-Dehydrocholesterol and Phytosterol, which is the 3rd crop. These solids obtained in 1st, 2nd and 3rd crops are reused in subsequent batches for the irradiation to obtain Vitamin D3.

The filtrate is then evaporated under vacuum at 40-45° C. and the crude Vitamin D3 (resin) is analysed and the results are shown in table 2.

In yet another preferred embodiment, 7-Dehydrocholesterol is charged with Lanosterol approximately in the ratio of 1:0.1 to 1:3 along with catalytic amounts of Butylated hydroxyl toluene as an anti-oxidant and 2 to 10% of Aq. Sodium hydroxide solution in Ethanol and heated the reaction mass at a temperature range of 0-90° C. preferably at 20-85° C. or more preferably 75-85° C. The reaction mass is then irradiated by a low pressure Mercury lamp at 80-85° C. for 30-300 minutes preferably 60-240 minutes or more preferably 100-200 minutes. The reaction mass is cooled to 10-15° C.

The solids separated out are filtered which contains 7-Dehydrocholesterol and Lanosterol which is the 1st crop.

The filtrate is concentrated to 5-50% of the original volume preferably 10-40% or more preferably 10-20% of the original volume, cooled to 10-15° C. and the separated solids are filtered that contains 7-Dehydrocholesterol and Lanosterol, which is the 2nd crop.

The filtrate is again concentrated under vacuum and methyl tert butyl ether is added and washed with 1:1 ethanol water and distilled under vacuum. 2-Butanone (methyl ethyl ketone) is added to the residue, cooled to (−5) to (−8)° C. and the separated solids are filtered which contains Vitamin D3, 7-Dehydrocholesterol and Lanosterol, which is the 3rd crop. These solids obtained in 1st, 2nd and 3rd crops are reused in subsequent batches for the irradiation to obtain Vitamin D3.

The filtrate is then evaporated under vacuum at 40-45° C. and the crude Vitamin D3 (resin) is analysed and the results are shown in table 3.

The Vitamin D3 (resin) thus obtained is purified by converting into its ester such as Acetate, Propionate, Butyrate, Valerate, 2-Nitrobenzoate, 4-Nitrobenzoate more preferably Butyrate, crystallized and finally saponified using a base selected from Sodium Hydroxide, Potassium hydroxide, Sodium carbonate, Potassium carbonate, Sodium methoxide, Sodium Ethoxide, Potassium butoxide or Lithium Aluminium Hydride and finally crystallized from acetone.

Alternately, the crude Vitamin D3 thus obtained can be purified by column chromatography using Silica gel or Alumina or Alumina with 2-10% water and using Toluene:2-Butanone as an eluent.

The present invention is exemplified by the following examples which are provided for illustration only and, should not be construed to limit the scope of the invention.

EXAMPLES

Example 1

96 gms of 7-Dehydrocholesterol, 90 gms of Cholesterol, 1 gm of Butylated hydroxyl toluene and 25 ml of 2% Aq. Sodium hydroxide solution were dissolved in 1250 ml of Ethanol at 75-85° C. and the mixture was irradiated by a LOW PRESSURE Mercury lamp at 80-85° C. for 180 minutes preferably. The reaction mass was cooled to 25-30° C. The solids separated out were filtered as first crop which contains 7-Dehydrocholesterol (50-60%)+Cholesterol.

The filtrate was concentrated to 20% of the original volume, cooled to 20-25° C. and the separated solids were filtered as second crop that contains 7-Dehydrocholesterol (15-20%)+Cholesterol.

The filtrate was again concentrated under vacuum. 2000 ml Methyl tert butyl ether was added, washed with 2*50 ml 1:1 ethanol water and distilled under vacuum. 3000 ml 2-Butanone (methyl ethyl ketone) was added to the residue, cooled to 10° C. and the separated solids were filtered as the third crop that contains Vitamin $D_3$ (5-MIU)+7-Dehydrocholesterol 20%+Cholesterol 20%.

All these first, second and third crops are combined and reused in subsequent batches.

The filtrate was then evaporated under vacuum at 40-45° C. and the crude Vitamin $D_3$ (resin) was analysed, as shown in table 1.

TABLE 1

| S no | Compound | % by HPLC | Potency |
|---|---|---|---|
| 1 | Vitamin $D_3$/Cholecalciferol + pre-Vitamin $D_3$ | 90-92% | 27-29 MIU |
| 2 | Cholesterol | 0.5-1.3% | NA |
| 3 | 7-Dehydrocholesterol | 0.5-1% | NA |
| 4 | Tachysterol | 1-2% | NA |
| 5 | Lumisterol | 1-2% | NA |
| 6 | Trans Vitamin $D_3$ | 0.5-1% | NA |

The crude resin thus obtained can be purified by either of the following methods:
1. Converting the resin to its ester like Acetate or Propionate or Butyrate or Valerate or 2-Nitrobenzoate or 4-Nitrobenzoate more preferably Butyrate, crystallized and finally saponified by a base like Sodium Hydroxide or Potassium hydroxide or Sodium carbonate or Potassium carbonate Sodium methoxide or Sodium Ethoxide or Potassium butoxide or Lithium Aluminium Hydride and finally crystallized from acetone.
2. Purification of the Crude resin by column chromatography using Silica gel or Alumina or Alumina with 2-10% water and using Toluene: 2-Butanone as an eluent.

Example 2

96 gms of 7-Dehydrocholesterol, 50 gms of Phytosterol, 1 gm of Butylated hydroxyl toluene and 20 ml of 2% Aq. Sodium hydroxide solution are dissolved in 1000 ml of Ethanol, at 75-85° C. and the mixture was irradiated by a low pressure mercury lamp at 80-85° C. for 30 minutes. The reaction mass was cooled to 35-40° C.

The solids separated out were filtered as a first crop that contains 7-Dehydrocholesterol (50-60%)+Phytosterol.

The filtrate was concentrated to 60% of the original volume, cooled to 25-30° C. and the separated solids were filtered as a second crop that contains 7-Dehydrocholesterol (15-20%)+Phytosterol.

The filtrate was again concentrated under vacuum. 2000 ml Methyl tert butyl ether was added washed with 2*50 ml 1:1 ethanol water and distilled under vacuum. 3000 ml 2-Butanone was added to the residue, cooled to (−5)-(−8)° C. and the separated solids were filtered as a third crop that contains Vitamin $D_3$ (5 MIU)+7-Dehydrocholesterol (20%)+Phytosterol (20%). All these first, second and third crops are combined and reused in subsequent batches.

The filtrate was then evaporated under vacuum at 40-45° C. and the crude Vitamin $D_3$ (resin) was analysed and the results are as shown in table 2.

TABLE 2

| S no | Compound | % by HPLC | Potency |
|---|---|---|---|
| 1 | Vitamin $D_3$/Cholecalciferol + pre-Vitamin $D_3$ | 88-90% | 23-24 MIU |
| 2 | Phytosterol | 2-3% | NA |
| 3 | 7-Dehydrocholesterol | 1-2% | NA |
| 4 | Tachysterol | 2-2.5% | NA |
| 5 | Lumisterol | 2-2.5% | NA |
| 6 | Trans Vitamin $D_3$ | 1-2% | NA |

The crude resin was purified by either of the following methods:
1. Converting the resin to its ester like Acetate or Propionate or Butyrate or Valerate or 2-Nitrobenzoate or 4-Nitrobenzoate more preferably Butyrate, crystallized and finally saponified by a base like Sodium Hydroxide or Potassium hydroxide or Sodium carbonate or Potassium carbonate Sodium methoxide or Sodium Ethoxide or Potassium butoxide or Lithium Aluminium Hydride and finally crystallized from acetone.
2. Purification of the Crude resin by column chromatography using Silica gel or Alumina or Alumina with 2-10% water and using Toluene: 2-Butanone as an eluent.

Example 3

96 gms of 7-Dehydrocholesterol, 200 gms of Lanosterol 1 gm of Butylated hydroxyl toluene and 1 ml of 2% Aq. Sodium hydroxide solution are dissolved in 6000 ml of Ethanol, at 75-85° C. and the mixture was then irradiated by a LOW PRESSURE mercury lamp at 80-85° C. for 285 minutes. The reaction mass was cooled to 30-35° C.

The solids separated out were filtered as first crop which contains 7-Dehydrocholesterol (50-60%)+Lanosterol The filtrate was concentrated to 50% of the original volume cooled to 25-30° C. and the separated solids were filtered as second crop that contains 7-Dehydrocholesterol (15-20%)+Lanosterol.

The filtrate was again concentrated under vacuum. 2000 ml Methyl tert butyl ether was added washed with 2*50 ml 1:1 ethanol water and distilled under vacuum. 3000 ml 2-Butanone (methyl ethyl ketone) was added to the residue, cooled to 15° C. and the separated solids were filtered to obtain third crop that contains Vitamin $D_3$ (15MIU)+7-Dehydrocholesterol 20%+Lanosterol 20%. All these first, second and third crops were combined and reused in subsequent batches.

The filtrate was then evaporated under vacuum at 40-45° C. and the crude Vitamin $D_3$ (resin) was analyzed and the results are shown in table 3.

TABLE 3

| S no | Compound | % by HPLC | Potency |
|---|---|---|---|
| 1 | Vitamin $D_3$/Cholecalciferol + pre-Vitamin $D_3$ | 85-90% | 28-30 MIU |
| 2 | Lanosterol | 2-3% | NA |
| 3 | 7-Dehydrocholesterol | 1.5-2% | NA |
| 4 | Tachysterol | 2-4% | NA |
| 5 | Lumisterol | 1-3% | NA |
| 6 | Trans Vitamin $D_3$ | 2-3% | NA |

The crude resin was purified by either of the following methods:
1. Converting the resin to its ester like Acetate or Propionate or Butyrate or Valerate or 2-Nitrobenzoate or 4-Nitrobenzoate more preferably Butyrate, crystallized and finally saponified by a base like Sodium Hydroxide or Potassium hydroxide or Sodium carbonate or Potassium carbonate Sodium methoxide or Sodium Ethoxide or Potassium butoxide or Lithium Aluminium Hydride and finally crystallized from acetone.
2. Purification of the Crude resin by column chromatography using Silica gel or Alumina or Alumina with 2-10% water and using Toluene: 2-Butanone as an eluent.

Example 4

96 gms of 7-Dehydrocholesterol, 104 gms of Cholesterol, 1 gm of Butylated hydroxyl toluene and 25 ml of 2% Aq. Sodium hydroxide solution are dissolved in 1250 ml of Ethanol at 75-85° C. and the mixture was then irradiated by a LOW PRESSURE Mercury lamp at 80-85° C. for 180 minutes preferably. The reaction mass was cooled to 25-30° C.

The solids separated out were filtered as first crop which contains 7-Dehydrocholesterol (50-60%)+Cholesterol.

The filtrate was concentrated to 20% of the original volume, cooled to 20-25° C. and the separated solids were filtered as second crop that contains 7-Dehydrocholesterol (15-20%)+Cholesterol.

The filtrate was again concentrated under vacuum. 2000 ml Methyl tert butyl ether was added washed with 2*50 ml 1:1 ethanol water and distilled under vacuum. 3000 ml 2-Butanone (methyl ethyl ketone) was added to the residue, cooled to 10° C. and the separated solids were filtered as the third crop that contains Vitamin $D_3$ (5-MIU)+7-Dehydrocholesterol 20%+Cholesterol 20%. All these first, second and third crops were combined and reused in subsequent batches.

The filtrate was then evaporated under vacuum at 40-45° C.

The residue was purified by column chromatography over silica gel with Toluene:methyl ketone 1:99, 2:98, 4:96 & 5:95 to isolate pure Vitamin $D_3$/Cholecalciferol crystals.

The HPLC analysis of the vitamin D3 crystals are shown in Table 4 as shown below.

TABLE 4

| S no | Compound | % by HPLC | Potency |
|---|---|---|---|
| 1 | Vitamin $D_3$/Cholecalciferol | 98-99.5% | 40 MIU |
| 2 | Cholesterol | ND | NA |
| 3 | 7-Dehydrocholesterol | ND | NA |
| 4 | Tachysterol | 0.01% | NA |
| 5 | Lumisterol | 0.01% | NA |
| 6 | Trans Vitamin $D_3$ | 0.05% | NA |

We claim:

1. A photochemical process for preparation of vitamin D3, which process comprises;
   a) heating a mixture of 7-dehydrocholesterol (7-DHC) and a sterol derivative with catalytic amounts of an anti-oxidant in presence of an alkali in an organic solvent at a temperature range of 20-85° C. to obtain a reaction mass;
   b) irradiating the reaction mass using a low pressure Mercury lamp at 10-85° C.; and
   c) isolating and purifying vitamin D3 from the irradiated reaction mass,
      wherein the sterol derivative is selected from the group consisting of cholesterol, phytosterol, and lanosterol.

2. The process as claimed in claim 1, wherein the organic solvent is selected from the group consisting of methanol, ethanol, isopropanol, tetrahydrofuran, diethyl ether, methyl-tert-butyl ether, methyl isobutyl ketone, and petroleum ether.

3. The process as claimed in claim 1, wherein, prior to irradiating, the 7-dehydrocholesterol and the sterol derivative are present in the mixture in a ratio of approximately 0.1:1 to 1:3.

4. The process as claimed in claim 1, wherein the anti-oxidant is selected from the group consisting of butylated hydroxyl toluene, propyl gallate, and butylated hydroxyanisole.

5. The process as claimed in claim 1, wherein the anti-oxidant is butylated hydroxyl toluene.

6. The process as claimed in claim 1, wherein the alkali is 2% to 10% of aqueous sodium hydroxide solution.

7. The process as claimed in claim 1, wherein the reaction mass is irradiated by a low pressure mercury lamp at 10-85° C. for 30-300 minutes to accomplish the reaction.

8. The process as claimed in claim 1, wherein the isolation and purification of vitamin D3 comprises the steps of;
   c1) repeatedly cooling the reaction mass to 0-45° C. to separate solids consisting of unreacted 7-DHC and unreacted sterol derivative followed by filtering the reaction mass under vacuum to obtain a first filtrate;
   c2) adding an organic solvent to the first filtrate, followed by washing the first filtrate with an aqueous alcohol and further distillation under vacuum to obtain a residue;
   c3) adding an organic solvent to the residue followed by cooling the residue to −5° C.-+35° C. to separate solids consisting of Vitamin D3 (5-10 MIU), 7-Dehydrocholesterol, and the sterol derivative;
   c4) filtering the mixture of the residue and the organic solvent to obtain a second filtrate and evaporating the second filtrate under vacuum at 40-45° C. to obtain crude Vitamin D3 (resin); and
   c5) purifying the crude vitamin D3 by converting the crude vitamin D3 into a vitamin D3 ester followed by saponification and crystallization of the vitamin D3 ester from an organic solvent to obtain pure vitamin D3.

9. The process as claimed in claim 8, wherein the solids consisting of unreacted 7-DHC and unreacted sterol derivative obtained in steps c1) and c3) are collected to reuse in a subsequent batch.

10. The process as claimed in claim 8, wherein the vitamin D3 ester is selected from the group consisting of acetate, propionate, butyrate, valerate, 2-nitrobenzoate, and 4-nitrobenzoate vitamin D3 esters.

11. The process as claimed in claim 8, wherein the saponification of the vitamin D3 ester is carried out using a base selected from the group consisting of sodium hydroxide, potassium hydroxide, sodium carbonate, potassium carbonate, sodium methoxide, sodium ethoxide, potassium butoxide, and lithium aluminium hydride.

12. The process as claimed in claim 8, wherein:
   the organic solvent used in step c2) is selected from the group consisting of methyl tert-butyl ether, petroleum ether, n-heptane, n-hexane, ethyl acetate, diethyl ether, toluene and xylene; and
   the aqueous alcohol is selected from the group consisting of aqueous methanol, aqueous ethanol, and aqueous isopropanol.

13. The process as claimed in claim 8, wherein the organic solvent used in step c3) is selected from the group consisting of 2-butanone, acetone, methyl-isobutyl ketone, petroleum ether, n-heptane, and n-hexane.

14. The process as claimed in claim 8, wherein the organic solvent used in step c5) is selected from the group consisting of acetone, 2-butanone, methyl isobutyl ketone, methyl formate, and ethyl formate.

15. The process as claimed in claim 8, wherein the residue obtained in step c2) is purified by column chromatography over silica gel/alumina or 2-10% hydrated alumina with a mobile phase comprising:
   toluene: 2-butanone in a ratio of 1:99 to 5:95; or
   dichloromethane: methanol in a ratio of 99:1 to 90:10, to isolate pure vitamin D3/cholecalciferol crystals.

16. The process as claimed in claim 1, wherein the alkali is selected from the group consisting of sodium hydroxide, potassium hydroxide, lithium hydroxide, and ammonia.

17. The process as claimed in claim 7, wherein the mixture is irradiated by a low pressure mercury lamp at 10-85° C. for 60-240 minutes to accomplish the reaction.

18. The process as claimed in claim 17, wherein the mixture is irradiated by a low pressure mercury lamp at 10-85° C. for 100-200 minutes to accomplish the reaction.

* * * * *